United States Patent
Ryu et al.

(10) Patent No.: US 9,956,242 B2
(45) Date of Patent: May 1, 2018

(54) PHARMACEUTICAL COMPOSITION FOR PREVENTION OR TREATMENT OF COGNITIVE FUNCTION DISORDERS COMPRISING SPINOSIN

(71) Applicants: MINISTRY OF FOOD AND DRUG SAFETY, Cheongwon-gun (KR); DAE HWA PHARMA. CO., LTD., Hoengseong-gun (KR)

(72) Inventors: Jong Hoon Ryu, Seoul (KR); Hyung Eun Lee, Seoul (KR); Sam Sik Kang, Seoul (KR); Ju Sun Kim, Seongnam-si (KR); So Young Lee, Seoul (KR); Do Hoon Kim, Seoul (KR); Dong Sup Kim, Seoul (KR); Seung Hee Kim, Seou (KR)

(73) Assignees: MINISTRY OF FOOD AND DRUG SAFETY, Cheongwon-gun (KR); DAE HWA PHARMA, CO., LTD., Hoengseong-gun (KR)

( * ) Notice: Subject to any disclaimer, the term of this patent is extended or adjusted under 35 U.S.C. 154(b) by 49 days.

(21) Appl. No.: 15/343,075

(22) Filed: Nov. 3, 2016

(65) Prior Publication Data
US 2017/0065627 A1    Mar. 9, 2017

Related U.S. Application Data

(62) Division of application No. 14/361,243, filed as application No. PCT/KR2012/010318 on Nov. 30, 2012, now abandoned.

(30) Foreign Application Priority Data

Nov. 30, 2011    (KR) .................. 10-2011-0127108

(51) Int. Cl.
| | | |
|---|---|---|
| A61K 31/7048 | (2006.01) | |
| A61K 36/185 | (2006.01) | |
| A61K 36/42 | (2006.01) | |
| A61K 36/47 | (2006.01) | |
| A61K 36/48 | (2006.01) | |
| A61K 36/725 | (2006.01) | |
| A23L 33/135 | (2016.01) | |
| A23L 33/10 | (2016.01) | |
| A23L 2/52 | (2006.01) | |

(52) U.S. Cl.
CPC ............ *A61K 31/7048* (2013.01); *A23L 2/52* (2013.01); *A23L 33/10* (2016.08); *A23L 33/135* (2016.08); *A61K 36/185* (2013.01); *A61K 36/42* (2013.01); *A61K 36/47* (2013.01); *A61K 36/48* (2013.01); *A61K 36/725* (2013.01); *A23V 2002/00* (2013.01)

(58) Field of Classification Search
None
See application file for complete search history.

(56) References Cited

U.S. PATENT DOCUMENTS

2015/0065441 A1    3/2015    Ryu et al. ................. 514/27

FOREIGN PATENT DOCUMENTS

| KR | 10-2005-0026806 | 3/2005 |
| KR | 10-2005-0047779 | 5/2005 |
| KR | 10-2005-0095819 | 10/2005 |
| KR | 10-2006-0034405 | 4/2006 |
| KR | 10-2011-0115330 | 10/2011 |

OTHER PUBLICATIONS

Liu et al., Talanta, 2007, vol. 71, pp. 668-675.*
Letter/Written Disclosure of the Information Disclosure Statement for the above-referenced application, filed herewith Dec. 20, 2016, 2 pages.
Akhondzadeh et al., "Melissa officinalis extract in the treatment of patients with mild to moderate Alzheimer's disease: a double blind, randomised, placebo controlled trial," J. Neurol. Neurosurg. Psychiatry 74:863-866 (2003).
Alzheimer's Association, "2009 Alzheimer's disease facts and figures," Alzheimers Dement. 5:234-270 (2009).
Cummings et al., "Behavioral effects of current Alzheimer's disease treatments: a descriptive review," Alzheimers Dement. 4:49-60 (2008).
Ebert et al., "Scopolamine model of dementia: electroencephalogram findings and cognitive performance," Eur. J. Clin. Invest., 28:944-949 (1998).
Hong et al., "Candidate anti-A beta fluorene compounds selected from analogs of amyloid imaging agents," Neurobiol. Aging 31(10): 1690-1699 (2010).
Hyman et al., "Alzheimer's disease: cell-specific pathology isolates the hippocampal formation," Science 225:1168-1170 (1984).
Jung et al., "Neuroprotective and memory enhancing effects of Semen Zizyphi Spinosae extract,"The Korea Journal of Herbology 20(1):19-33 (2005) [English abstract].
Kar et al., "Interactions between beta-amyloid and central cholinergic neurons: implications for Alzheimer's disease," J. Psychiatry Neurosci. 29(6):427-441 (2004).
Kawashima et al., "Pharmacological Properties of Traditional Medicines. XXIII. Searching for Active Compounds in the Blood and Bile of Rats after Oral Administration of Extracts of Sansohnin," Biol. Pharm. Bull. 20(11): 1171-1174 (1997).
Liu et al., "Simultaneous analysis and identification of main bioactive constituents in extract of *Zizyphus jujuba* var. *sapinosa* (Zizyphi spinosi semen) by high-performance liquid chromatography photodiode array detection electrospray mass spectrometry," Talanta 71:668-675 (2007).
Machine-generated English language translation of Korean Patent Publication No. KR 10-2005-0026806, Korean Intellectual Property Office, 14 pages.
Machine-generated English language Translation of Korean Patent Publication No. KR 10-2005-0047779, Korean Intellectual Property Office, 21 pages.

(Continued)

*Primary Examiner* — Traviss C McIntosh, III
(74) *Attorney, Agent, or Firm* — Dentons US LLP; Stephanie Seidman (57) ABSTRACT

The pharmaceutical composition of the present invention, which comprises spinosin or a spinosin-containing herbal extract, is a composition for preventing and treating cognitive function disorders, and can effectively improve memory and learning ability, and effectively treat and prevent cognitive function disorders such as dementia and amnesia.

5 Claims, 5 Drawing Sheets

(56) References Cited

OTHER PUBLICATIONS

Machine-generated English language Translation of Korean Patent Publication No. KR 10-2005-0095819, Korean Intellectual Property Office, 22 pages.
Machine-generated English language Translation of Korean Patent Publication No. KR 10-2006-0034405, Korean Intellectual Property Office, 18 pages.
Machine-generated English language Translation of Korean Patent Publication No. KR 10-2011-0115330, Korean Intellectual Property Office, 28 pages.
Ramassamy et al., "Emerging role of polyphenolic compounds in the treatment of neurodegenerative diseases: A review of their intracellular targets," European Journal of Pharmacology 545:51-64 (2006).
Sorter et al., "Attenuation of scopolamine-induced impairment of spontaneous alteration behaviour by antagonist but not inverse agonist and agonist beta-carbolines," Psychopharmacology 94:491-495 (1988).
Terry A.V. and J.J. Buccafusco, "The cholinergic hypothesis of age and Alzheimer's disease-related cognitive deficits: recent challenges and their implications for novel chug development," J. Pharmacol. Exp. Ther. 306(3):821-827 (2003).
Voss and Paller, "Brain substrates of implicit and explicit memory: The importance of concurrently acquired neutral signals of both memory types," Neuropsychologia 46(13):3021-3029 (2008).
Whitehouse et al., "Alzheimer's disease and senile dementia: loss of neurons in the basal forebrain," Science 215:1237-1239 (1982).
International Search Report and Written Opinion, dated Mar. 28, 2013, in connection with corresponding International Patent Application No. PCT/KR2012/010318 [English translation], 8 pages.
International Preliminary Report on Patentability, dated Jun. 3, 2014, in connection with corresponding International Patent Application No. PCT/KR2012/010318 [English translation], 7 pages.
Extended European Search Report, dated Apr. 1, 2015, in connection with corresponding European Patent Application No. 12853870.9, 5 pages.
Office Action, dated Sep. 24, 2015, in connection with U.S. Appl. No. 14/361,243, 12 pages.
Response, submitted Oct. 16, 2015, to Extended European Search Report, dated Apr. 1, 2015, in connection with corresponding European Patent Application No. 12853870.9, 10 pages.
Response, submitted Jan. 25, 2016, to Office Action, dated Sep. 24, 2015, in connection with U.S. Appl. No. 14/361,243, 10 pages.
Final Office Action, dated May 4, 2016, in connection with U.S. Appl. No. 14/361,243, 10 pages.
Communication Pursuant to Article 94(3) EPC, dated Jul. 1, 2016, in connection with corresponding European Patent Application No. 12853870.9, 5 pages.
Response, filed Nov. 9, 2016, to Communication Pursuant to Article 94(3) EPC, dated Jul. 1, 2016, in connection with European Patent Application No. 12853870.9, 42 pages.
Letter/Written Disclosure of the Supplemental Information Disclosure Statement for the above-referenced application, filed herewith Jun. 27, 2017, 2 pages.
"Inhibition effect of MMSE decrease similar to donepezil hydrochloride," Medical ASAHI 37(3):85-87 (2008) [Partial English translation and original document in Japanese], 6 pages.
Office Action, dated Jun. 23, 2015, in connection with Japanese Patent Application No. 544675/2014 [English translation and original document in Japanese], 6 pages.

\* cited by examiner

PHARMACEUTICAL COMPOSITION FOR PREVENTION OR TREATMENT OF COGNITIVE FUNCTION DISORDERS COMPRISING SPINOSIN

CROSS-REFERENCE TO RELATED APPLICATION

This application is a divisional of co-pending U.S. patent application Ser. No. 14/361,243, titled "PHARMACEUTICAL COMPOSITION FOR PREVENTION OR TREATMENT OF COGNITIVE FUNCTION DISORDERS COMPRISING SPINOSIN," filed May 28, 2014 with a 371(c) date of Oct. 13, 2014, which is the U.S. national stage of PCT/KR2012/010318, titled "PHARMACEUTICAL COMPOSITION FOR PREVENTION OR TREATMENT OF COGNITIVE FUNCTION DISORDERS COMPRISING SPINOSIN," having an international filing date of Nov. 30, 2012, which claims priority to Korean patent application number 10-2011-0127108, filed Nov. 30, 2011, the specification of each of which is incorporated by reference herein in its entirety.

TECHNICAL FIELD

The present invention relates to a pharmaceutical composition comprising spinosin for prevention and treatment of cognitive impairments. More particularly, the present invention relates to a pharmaceutical composition which can improve memory and learning ability, thus effectively preventing and treating disorders such as dementia and amnesia.

BACKGROUND ART

With the development of medical technology and the improvement of living standards, the average lifespan of a human has been almost doubled over the past half century, and thus the ratio of the elderly population to the total population has increased rapidly. Along with the development of an aging society, senile dementia has emerged as one of the major health problems that need to be addressed in the twenty-first century. Therefore, the need to develop functional materials, foods, etc. that can prevent and treat cognitive impairments including dementia has been increasing.

Dementia that is a typical disease of cognitive impairments is a pathological condition that needs to be distinguished from normal aging and is classified into Alzheimer's disease, vascular dementia, and other dementias caused by alcoholism, trauma, sequelae of Parkinson's disease, etc.

It has been reported that Alzheimer's disease is one of chronic psychiatric disorders including disorders of higher cerebral functions such as loss of memory, impaired consciousness, spatiotemporal chaos, thinking ability, arithmetic ability, judgment, common sense, etc. Moreover, it has been reported that Alzheimer's disease also occurs in relatively young people and most frequently occurs in elderly people as the incidence is increased two times for each increase of 5 years in the range of 65 to 85 years old. While the pathogenesis of Alzheimer's disease is not clearly known, a decrease in acetylcholine function in the central nervous system most commonly occurs, and thus therapeutic methods of administering acetylcholine precursors or drugs that inhibit the degradation of acetylcholine to increase the concentration of acetylcholine in the brain have been used. Therefore, acetylcholinesterase (hereinafter, 'AChE') inhibitors have been used alone or in combination with existing cholinesterase inhibitors, and examples of such drugs include tacrine, donepezil, rivastigmine, galantamine, etc. While these drugs are acetylcholinesterase inhibitors, they only slow the progression of diseases, but have little effect on the treatment and have limited therapeutic potential at the beginning of the disease, and thus made efforts have been made to develop drugs that treat the underlying cause of Alzheimer's disease (Terry and Buccafusco, 2003; Kar et al., 2004; Akhondzadeh et al., 2008; Cummings et al., 2008; Voss et al., 2008).

Vascular dementia is mostly caused by damage to the brain cells due to lack of blood supply to certain parts of the brain caused by cerebral arteriosclerosis. The causes of the vascular dementia and Alzheimer's disease are different, but they are the same in that they cause damage to memory and learning ability.

Accordingly, the present inventors have studied to develop an effective medicine for prevention or treatment of cognitive impairments such as dementia and found herbal extracts and their active ingredients which can effectively improve memory and learning ability, thus completing the present invention.

PRIOR ART LITERATURES

Patent Literatures

KR 10-2010-0034779;
KR 10-2004-0083414;
KR 10-2003-0062963.

Non-Patent Literatures

2009 Alzheimer's disease facts and figures, Alzheimer's Dement (2009) 5(3): p. 234-70;
Whitehouse, P. J., Price, D. L., Struble, R. G., Clark, A. W., Coyle, J. T., and Delong, M. R. (1982) Alzheimer's disease and senile dementia: loss of neurons in the basal forebrain. Science 215, 1237-12392;
Hyman, B. T., Van Hoesen, G. W., Damasio, A. R., and Barnes, C. L. (1984) Alzheimer's disease: cell-specific pathology isolates the hippocampal formation. Science 225, 1168-11703.

DISCLOSURE

Technical Problem

An object of the present invention is to provide a pharmaceutical composition comprising spinosin for prevention or treatment of cognitive impairments.

Another object of the present invention is to provide a pharmaceutical composition comprising a spinosin-containing herbal extract for prevention or treatment of cognitive impairments.

Still another object of the present invention is to provide a food composition comprising spinosin for prevention or improvement of cognitive impairments.

Yet another object of the present invention is to provide a food composition comprising a spinosin-containing herbal extract for prevention or improvement of cognitive impairments.

Still yet object of the present invention is to provide a pharmaceutical composition comprising spinosin for prevention or treatment of degenerative brain diseases.

A further object of the present invention is to provide a pharmaceutical composition comprising a spinosin-containing herbal extract for prevention or treatment of degenerative brain diseases.

Another further object of the present invention is to provide a method for preventing or treatment of cognitive impairments or degenerative, brain diseases, the method comprising administering to a subject in need thereof a composition comprising spinosin.

Technical Solution

The present invention relates to a pharmaceutical composition comprising spinosin for prevention or treatment of cognitive impairments.

Spinosin (6-(2-O-beta-D-Glocopyranosyl-beta-D-glucopyranosyl)-5-hydroxy-2-(4-hydroxyphenyl)-7-methoxy-4H-1-benzopyran-4-one) is a compound represented by the following formula 1:

[Formula 1]

Spinosin represented by the above formula 1 can prevent or treat cognitive impairments. More particularly, the spinosin represented by the above formula 1 can improve memory and learning ability, thus effectively preventing and treating cognitive impairments.

The pharmaceutical composition comprising spinosin of the present invention can significantly improve learning ability, space perception ability, and memory in animal models with memory impairment induced by scopolamine, and thus exhibits excellent activity in the prevention or treatment of cognitive impairments and is particularly useful for the improvement of dementia and amnesia.

Spinosin represented by the above formula 1 may be obtained from various types of herbal medicines. For example, the spinosin represented by the above formula 1 may be obtained from Zizyphus jujuba Mill var. inermis, Zizyphus jujuba Mill var. hoonensis, Zizyphus jujuba Mill var. spinosa, Passiflora edulis flavicarpa, Cayaponia tayuya, Desmodium tortuosum, Wilbrandia ebracteata, Strophioblachia fimbricalyx, Clutia abyssinica, Saccharopolyspora spinosa, or mixtures thereof, and may preferably be obtained from zizyphi spinosi semen, the seeds of Zizyphus jujuba Mill var. spinosa.

Spinosin represented by the above formula 1 may be obtained from an extract of the above-described herbal medicines or mixtures thereof, and the spinosin represented by the above formula 1 may preferably be obtained from a water, methanol, ethanol, butanol, or hexane extract of the above-described herbal medicines or mixtures thereof. For example, the spinosin represented by the above formula 1 may be obtained from an extract of zizyphi spinosi semen, the seeds of Ziziphus jujuba Mill var. spinosa.

Preferably, the spinosin represented by the above formula 1 may be obtained from an extract of an ethanol extract of zizyphi spinosi semen, the seeds of Zizyphus jujuba Mill var. spinosa.

Otherwise, Spinosin represented by the above formula 1 may be commercially available.

According to the present invention, the cognitive impairments refer to diseases caused by impaired functions such as memory, space perception ability, judgment, executive function, linguistic ability, etc. and may include, for example, Alzheimer's disease, vascular dementia, other dementias caused by various factors alcoholism, trauma, sequelae of Parkinson's disease, etc., or amnesia. Preferably, the cognitive impairment may be Alzheimer's disease.

The pharmaceutical composition comprising spinosin of the present invention can effectively inhibit scopolamine-induced memory impairments in mice even with a small amount.

The spinosin is an ingredient contained in the above-described herbal medicines and can effectively prevent or treat cognitive impairments without side effects.

In the pharmaceutical composition comprising spinosin for prevention or treatment of cognitive impairments according to the present invention, the spinosin may be administered once or several times at a daily dose of about 1 mg to 120 mg for an adult, preferably at a daily dose of 30 mg to 120 mg. However, the dose of the spinosin can be appropriately adjusted depending on the condition of a patient, such as the patient's severity, age, sex, weight, etc., and the formulation, administration route, and administration period.

The present invention relates to a pharmaceutical composition for prevention and treatment of cognitive impairments, comprising spinosin represented by the above formula 1 and an extract of Zizyphus jujuba Mill var. inermis, Zizyphus jujuba Mill var. hoonensis, Zizyphus jujuba Mill var. spinosa, Passiflora edulis flavicarpa, Cayaponia tayuya, Desmodium tortuosum, Wilbrandia ebracteata, Strophioblachia fimbricalyx, Clutia abyssinica, Saccharopolyspora spinosa, or mixtures thereof.

The above-mentioned Zizyphus jujuba Mill var. inermis, Zizyphus jujuba Mill var. hoonensis, Zizyphus jujuba Mill var. spinosa, Passiflora edulis flavicarpa, Cayaponia tayuya, Desmodium tortuosum, Wilbrandia ebracteata, Strophioblachia fimbricalyx, Clutia abyssinica, and Saccharopolyspora spinosa comprise spinosin represented by the above formula 1. Therefore, the composition comprising an extract of the above-described herbal medicines can prevent or treat cognitive impairments, like the spinosin, and has no side effects because it is a herbal extract.

The pharmaceutical composition of the preset invention may comprise an extract of Zizyphus jujuba Mill var. spinosa, preferably a water, hexane, ethanol, methanol, butanol, or the mixture thereof extract of the seeds of Ziziphus jujuba Mill var. spinosa, more preferably an ethanol extract.

The spinosin-containing herbal extract can effectively prevent or treat cognitive impairments without side effects.

The herbal extract of the present invention comprises spinosin and thus can significantly improve learning ability, space perception ability, and memory in animal models with memory impairment induced by scopolamine, and thus exhibits excellent activity in prevention or treatment of cognitive impairments and is particularly useful for the improvement of dementia and amnesia.

The pharmaceutical composition of the present invention may comprise the herbal extract in an amount of 0.1 to 50 wt % with respect to the total weight of the composition. However, the content is not necessarily limited thereto, but may vary depending on the patient's condition and the type and progression of the disease.

In the pharmaceutical composition comprising a herbal extract for prevention or treatment of cognitive impairments according to the present invention, the herbal extract may be administered once or several times at a daily dose of about 10 mg to 1200 mg for an adult, preferably at a daily dose of 300 mg to 1200 mg. However, the dose of the herbal extract may be appropriately adjusted depending on the condition of a patient, such as the patient's severity, age, sex, weight, etc., and the formulation, administration route, and administration period.

The pharmaceutical composition comprising the spinosin represented by the above formula 1 or the spinosin-containing herbal extract has no toxicity and side effects and thus can be used with confidence even when taken for a long time for the purpose of prevention or treatment.

The present invention relates to a pharmaceutical composition comprising a pharmaceutically acceptable salt of spinosin for prevention or treatment of cognitive impairments or degenerative brain diseases. The term "pharmaceutically acceptable salt" refers to salts commonly used in the pharmaceutical industry, such as inorganic ion salts formed with potassium, sodium, magnesium, etc., inorganic acid salts formed with hydrochloric acid, nitric acid, phosphoric acid, bromic acid, iodic acid, perchloric acid, tartaric acid, sulfuric acid, etc., organic acid salts formed with acetic acid, trifluoroacetic acid, citric acid, maloic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc., sulfonic acid salts formed with methanesulfonic acid, ethanesulfonic acid, benzenesulfonic acid, p-toluenesulfonic acid, naphthalenesulfonic acid, etc., amino acid salts formed with glycine, arginine, lysine, etc., and amine salts formed with trimethylamine, triethylamine, ammonia, pyridine, picoline, etc., but the types of salts used in the present invention are not limited to the above-mentioned salts.

The cognitive impairments may be dementia or amnesia, and the degenerative brain diseases may be Parkinson's disease, stroke, stroke, or Huntington's disease.

The pharmaceutical composition of the present invention may further comprise pharmaceutically acceptable additives such as diluents, binders, disintegrants, lubricants, pH-adjusting agents, antioxidants, and solubilizers within the range where effects of the present invention are not impaired.

The diluents may include sugar, starch, microcrystalline cellulose, lactose (lactose hydrate), glucose, D-mannitol, alginate, alkaline earth metal salt, clay, polyethylene glycol, calcium anhydrous hydrogen phosphate, and mixtures thereof; and the binders may include starch, microcrystalline cellulose, highly dispersive silica, mannitol, D-mannitol, sucrose, lactose hydrate, polyethylene glycol, polyvinylpyrrolidone (povidone), polyvinylpyrrolidone copolymer (copovidone), hypromellose, hydroxypropylcellulose, natural gum, synthetic gum, copovidone, gelatin, and mixtures thereof.

The disintegrants may include starches or modified starches such as sodium starch glycolate, corn starch, potato starch, pregelatinized starch, etc.; clays such as bentonite, montmorillonite, veegum, etc.; celluloses such as microcrystalline cellulose, hydroxypropylcellulose, carboxymethylcellulose, etc.; algins such as sodium alginate, alginic acid, etc.; crosslinked celluloses such as croscarmellose sodium, etc.; gums such as guar gum, xanthan gum, etc.; crosslinked polymers such as crosslinked polyvinylpyrrolidone (crospovidone), etc.; effervescent agents such as sodium bicarbonate, citric acid, etc.; and mixtures thereof.

The lubricants may include talc, stearic acid, magnesium stearate, calcium stearate, sodium lauryl sulfate, hydrogenated vegetable oil, sodium benzoate, sodium stearyl fumarate, glyceryl behenate, glyceryl monorate, glyceryl monostearate, glyceryl palmitostearate, colloidal silicon dioxide, and mixtures thereof.

The pH-adjusting agents may include acidifying agents such as acetic acid, adipic acid, ascorbic acid, sodium ascorbate, sodium etherate, malic acid, succinic acid, tartaric acid, fumaric acid, and citric acid, and basifying agents such as precipitated calcium carbonate, aqueous ammonia, meglumine, sodium carbonate, magnesium oxide, magnesium carbonate, sodium citrate, and tribasic calcium phosphate.

The antioxidants may include dibutyl hydroxy toluene, butylated hydroxyanisole, tocopherol acetate, tocopherol, propyl gallate, sodium hydrogen sulfite, and sodium pyrosulfite. The solubilizers that may be used in a prior-release compartment of the present invention may include sodium lauryl sulfate, polyoxyethylene sorbitan fatty acid esters such as polysorbate, docusate sodium, poloxamer, etc.

For oral administration, the pharmaceutical composition comprising spinosin or the spinosin-containing herbal extract according to the present invention may be formulated into solid dosage forms such as tablets, pills, powders, granules, capsules, etc., and these solid dosage forms may be prepared by mixing spinosin or the spinosin-containing herbal extract with one or more excipients such as starch, calcium carbonate, sucrose or lactose, gelatin, etc. Moreover, lubricants such as magnesium stearate, talc, etc. may be used in addition to simple excipients. Furthermore, the pharmaceutical composition may be formulated into liquid dosage forms such as suspensions, liquid for internal use, emulsions, syrups, etc., and various excipients such as humectants, sweeteners, aromatics, preservatives, etc. in addition to water and liquid paraffin may be used for the formulation of the liquid dosage forms.

For parenteral administration, the pharmaceutical composition comprising spinosin or the spinosin-containing herbal extract according to the present invention may include sterile aqueous solutions, non-aqueous solvents, suspensions, emulsions, lyophilized preparations, and suppositories. Suitable non-aqueous solutions and suspensions may include propylene glycol, polyethylene glycol, vegetable oils such as olive oil, and injectable esters such as ethyl oleate. Bases for the suppositories may include Witepsol, macrogol, Tween 61, cacao butter, laurin butter, glycerogelatine, etc.

As used herein the term "administration" refers to the introduction of the composition for prevention and treatment of cognitive impairments according to the present invention to a patient in any appropriate way, and the composition for prevention and treatment of cognitive impairments according to the present invention may be administered via any conventional administration route as long as the composition can reach a target tissue. For example, the composition may be administered orally, intraperitoneally, intravenously, intramuscularly, subcutaneously, intradermally, intranasally, intrapulmonary, rectally, intracavitary, intraperitoneally, or intradurally, but not limited thereto. For example, the composition may be administered by oral, rectal, or intravenous, intramuscular, subcutaneous, endometrial, or intracerebroventricular injection.

The pharmaceutical composition according to the present invention may be administered once or several times a day at regular intervals.

The pharmaceutical composition according to the present invention may further comprise other active ingredients effective for the treatment of the cognitive impairments.

The pharmaceutical composition according to the present invention may be used alone or in combination with various methods such as hormone therapy, drug therapy, etc., for the prevention or treatment of the cognitive impairments.

The present invention relates to a food composition comprising spinosin represented by the above formula 1, a pharmaceutically acceptable salt thereof, or a spinosin-containing herbal extract for prevention or improvement of the cognitive impairments.

The food composition according to the present invention may further comprise additives commonly used in food compositions, health functional foods, or beverages.

For example, the food composition of the present invention may comprise sweeteners such as white sugar, crystalline fructose, glucose, D-sorbitol, mannitol, isomaltooligosaccharide, stevioside, aspartame, acesulfame potassium, sucralose, etc., acidifiers such as anhydrous citric acid, DL-malic acid, succinic acid, and salts thereof, preservatives such as benzoic acid and derivatives thereof, various nutrients, vitamins, minerals (electrolyte), flavoring agents such as synthetic and natural flavoring agents, coloring agents and fillers (cheese, chocolate, etc.), pectic acid and salts thereof, alginic acid and salts thereof, organic acids, protective colloidal thickeners, pH-adjusting agents, stabilizers, preservatives, glycerin, alcohol, carbonators used in carbonated drinks, etc. Moreover, the food composition of the present invention may comprise fruit pulp for preparation of natural fruit juices and vegetable juices. This additive may be used in an amount of less than about 20 parts by weight with respect to 100 parts by weight of the food composition.

When the food composition of the present invention is a beverage, it may further comprise flavoring agents or natural carbohydrates. Suitable natural carbohydrates may include monosaccharides such as glucose and fructose, disaccharides such as maltose and sucrose, polysaccharides such as dextrin and cyclodextrin, and sugar alcohols such as xylitol, sorbitol, and erythritol. Moreover, suitable flavoring agents may include natural flavoring agents such as thaumatin and *stevia* extracts (rebaudioside A, glycyrrhizin, etc.) and synthetic flavoring agents such as saccharin and aspartame. When the food composition is a beverage, the natural carbohydrate may be contained in an amount of about 1 to 20 g, preferably about 5 to 12 g with respect to 100 mL of the composition.

The food composition comprising spinosin or the spinosin-containing herbal extract according to the present invention may be prepared in the form of powders, granules, tablets, capsules, or beverages and used as foods, beverages, gums, teas, vitamin complexes, health supplement foods, etc.

The composition comprising spinosin or the spinosin-containing herbal extract according to the present invention may be added to drugs, foods, beverages, etc. for prevention and treatment of the cognitive impairments. For example, the composition comprising spinosin or the spinosin-containing herbal extract according to the present invention may be added to food, beverages, gums, teas, vitamin complexes, health supplement foods, etc.

The food composition comprising spinosin or the spinosin-containing herbal extract according to the present invention may be added to foods or beverages for prevention or improvement of the cognitive impairments. The composition of the present invention may be added in an amount of 1 to 5 wt % with respect to the total weight of the food and may be added in an amount of 0.02 to 10 q, preferably 0.3 g to 1 g, with respect to 100 mL of the beverage.

The present invention provides a pharmaceutical composition comprising spinosin for prevention or treatment of a degenerative brain diseases. The spinosin represented by the above formula 1 can effectively prevent or treat cerebral infarction, stroke, Parkinson's disease, or Huntington's disease.

The present invention provides a pharmaceutical composition comprising a spinosin-containing herbal extract for prevention or treatment of degenerative brain diseases. The spinosin-containing herbal extract can effectively prevent or treat cerebral infarction, stroke, Parkinson's disease, or Huntington's disease. The herbal extract may be obtained from *Zizyphus jujuba* Mill var. *inermis*, *Zizyphus jujuba* Mill var. *hoonensis*, *Zizyphus jujuba* Mill var. *spinosa*, *Passiflora odulis flavicarpa*, *Cayaponia tayuya*, *Desmodium tortuosum*, *Wilbrandia ebracteata*, *Strophioblachia fimbricalyx*, *Clutia abyssinica*, *Saccharopolyspora spinosa*, or mixtures thereof, and may preferably be obtained from the seeds of *Zizyphus jujuba* Mill var. *spinosa*.

The present invention provides a method for preventing or treatment of cognitive impairments or degenerative brain diseases, the method comprising administering to a subject in need thereof a composition comprising spinosin or a pharmaceutically acceptable salt thereof. The cognitive impairments may be dementia or amnesia, and the degenerative brain diseases may be cerebral infarction, stroke, Parkinson's disease, or Huntington's disease.

The present invention provides a method for preventing or treatment of cognitive impairments or degenerative brain diseases, the method comprising administering to a subject in need thereof a composition comprising a spinosin-containing herbal extract. The herbal extract may be obtained from *Zizyphus jujuba* Mill var. *inermis*, *Zizyphus jujuba* Mill var. *hoonensis*, *Zizyphus jujuba* Mill var. *spinosa*, *Passiflora edulis flavicarpa*, *Cayaponia tayuya*, *Desmodium tortuosum*, *Wilbrandia ebracteata*, *Strophioblachia fimbricalyx*, *Clutia abyssinica*, *Saccharopolyspora spinosa*, or mixtures thereof, and may preferably be obtained from the seeds of *Zizyphus jujuba* Mill var. *spinosa*.

Advantageous Effects

The pharmaceutical composition comprising spinosin or a spinosin-containing herbal extract according to the present invention can effectively prevent or treat cognitive impairments. Specifically, the pharmaceutical composition comprising spinosin or the spinosin-containing herbal extract according to the present invention can significantly improve memory and learning ability, thus effectively prevent or treat dementia.

DESCRIPTION OF DRAWINGS

FIG. 1 shows the latency time for the mice in drug administration groups 1 to 4, to which the spinosin prepared in Example 2 was administered.

FIGS. 2 to 5 show the effect of a pharmaceutical composition comprising a spinosin-containing zizyphi spinosi semen extract according to the present invention on the improvement of memory and learning ability.

MODE FOR INVENTION

Hereinafter, the present invention will be described in detail with reference to the following Examples and Experimental Examples. However, the following Examples and Experimental Examples are merely illustrative of the present invention and the present invention is not limited by the following Examples and Experimental Examples.

Moreover, all reagents and solvents mentioned below were purchased from Sigma unless otherwise stated, and optical rotations were measured using a JASCO P-1020 polarimeter. UV spectra were measured using a Hitachi JP/U3010, IR spectra were measured using a JASCO FT/IR-5300, NMR spectra was measured using a Bruker Avance 400 (400 MHz), and FAB Mass spectra were measured using a JECI, JMS-700 mass spectrometer.

Example 1

Preparation of Spinosin-Containing Zizyphi Spinosi Semen Extract 12 kg of zizyphi spinosi semen (the seeds of *Ziziphus jujuba* Mill var. *spinosa* Hu ex A.F. Chou) was crushed by a crusher and distributed into extraction bottles, n-hexane was added to the crushed zizyphi spinosi semen until it covered the surface of the crushed zizyphi spinosi semen, and the mixture was left to stand at room temperature for 3 days and then filtered. The hexane extracts were combined and concentrated when the hexane solutions were transparent after the same method was repeated four times.

After the removal of the hexane extracts, 70% ethanol was added to the remaining zizyphi spinosi semen until it covered the surface of zizyphi spinosi semen, and the mixture was left to stand at room temperature for 3 days and then filtered and concentrated under reduced pressure. 70% (v/v) ethanol was added to the residue and then extracted in water bath, followed by filtration and concentration. The extraction was performed 6 times by the method of adding 70% (V/v) ethanol and then extraction in water bath and filtration, and all the extracts were combined and concentrated under reduced pressure, yielding 70% (v/v) ethanol soft ext. of zizyphi spinosi semen.

Example 2

Isolation and Purification of Spinosin n-hexane, methanol, and water were added at a volume ratio of 10:9:1 to the ethanol soft ext. of zizyphi spinosi semen prepared in the above Example 1, the mixture was shaken and left to stand overnight to remove the hexane soluble fraction, and then the 90% methanol fraction was concentrated under reduced pressure. Distilled water was added to the concentrated 90% (v/v) methanol fraction, ethyl acetate in an amount equivalent to the distilled water was added, and then the ethyl acetate fraction was removed. n-butanol of an equivalent amount was added to the water layer, and then the n-butanol fraction was concentrated under reduced pressure.

The n-butanol fraction obtained by concentration under reduced pressure was loaded onto silica gel column and subjected to chromatography (7:1:0.5→7:1.5:0.5→7:2:0.5 MeOH) with solutions of methylene chloride, methanol, and water at volume ratios of 7:1:0.5, 7:1.5:0.5, and 7:2:0.5 and methanol as an eluent to obtain thirty small fractions, and the $25^{th}$ small fraction containing spinosin was obtained from the thirty small fractions by performing TLC.

The $25^{th}$ small fraction was loaded onto silica gel column and subjected to chromatography (100:8:6→100:10:7.5→100:12:9) with solutions of ethyl acetate, methanol, and water at volume ratios of 100:8:6, 100:10:7.5, 100:12:9 as an eluent to obtain small fractions, and the $3^{rd}$ small fraction containing spinosin was obtained from the small fractions by performing TLC.

The $3^{rd}$ small fraction was recrystallized with methanol to yield spinosin (3.2 g) as a pale yellow amorphous powder (yield: 0.027%).

The physicochemical properties of the spinosin were as follows:

TLC Rf: 3.27 (absorbent: silica gel $GF_{254}$, developing solvent: chloroform/methanol/water (520:280:80), color reagent: 20% sulfuric acid solution)

Melting point: 237-240° C.

$[\alpha]_b^{24}=-47.5°$ (c=0.01, MeOH)

UV, $\lambda_{max}$ (log ε) (MeOH) 216 (sh, 4.74), 272 (4.46), 334 (4.52) nm

IR, $U_{max}$ 3141 (OH), 1649, 1603, 1484, 1453, 1347, 1196, 1054, 1020, 841 $cm^{-1}$ $^1$H-NMR (400 MHz, DMSO-$d_6$+$D_2O$) δ: 2.56 (1H, dt, J=9.0 Hz, H-5'''), 2.74 (1H, dt, J=9.4 Hz, H-5'''), 2.83 (2H, t, J=8.3, H-2'''), 2.93 (2H, br d, 9.4 Hz, H-6'''), 2.94, 2.99 (1H each, t, J=8.5 Hz, H-4'''), 3.39 (2H, br d, J=12.1 Hz, H-6''), 3.70 (2H, t, J=9.0 Hz, H-3'''), 3.88 (6H, s, $OCH_3$), 4.15 (2H, d, J=7.8, H-1'''), 4.28, 4.45 (1H each, t, J=9.3 Hz, H-2''), 4.68 (2H, d, J=9.8 Hz, H-1''), 6.77, 6.79 (1H each, s, H-8), 6.80 (2H, s, H-3), 6.94 (4H, d, J=8.6 Hz, H-3',5'), 7.95 (4H, d, J=8.6 Hz, H-2',6'), 13.5, 13.6 (1H each, s, 5-OH)

$^{13}$C-NMR (100 MHz, DMSO-$d_6$+$D_2O$) δ: 56.5, 56.9 ($OCH_3$), 60.2, 60.8 (C-6'''), 61.6 (C-6''), 69.3, 69.6 (C-4''), 70.6 (C-4''), 71.1, 71.4 (C-1''), 74.7, 74.8 (C-2'''), 76.4 (C-3'''), 76.6, 76.8 (C-5'''), 78.4, 78.7 (C-3''), 80.9, 81.3 (C-2'''), 81.7, 82.0 (C-5''), 90.8, 91.3 (C-8), 103.4, 103.5 (C-3), 104.5, 104.7 (C-10), 105.4, 105.6 (C-1'''), 108.8 (C-6), 116.4 (C-3',5'), 121.4, 121.5 (C-1'), 128.9 (C-2',6'), 157.4, 157.5 (C-9), 159.6, 160.5 (C-5), 161.4 (C-4'), 164.2 (C-2), 164.3, 165.4 (C-7), 182.3, 182.6 (C-4)

Positive FAB-MS m/z 609 $[M+H]^+$

Experimental Example

Determination of Effect on Dementia Treatment

Experiments were performed using models with memory impairment induced by scopolamine to determine the effect of the spinosin and the zizyphi spinosi semen extract containing spinosin as an active ingredient prepared in Examples 1 and 2, and the detailed experimental methods are as follows:

1) Preparation of Experimental Animals 6-week-old ICR mice (Orient Bio Inc., Korea), weighing about 26 to 28 g, were fed with water and food freely available for 5 days in an environment, where the temperature was about 23±2° C., the humidity was about 55±10%, and the light-dark cycle was 12 hours (Animal Laboratory at the College of Pharmacy in Kyung Hee university), and used in the experiments.

2) Statistical Analysis

Statistical analysis of all experimental data was performed using a one-way analysis of variance (ANOVA), and when the statistical significance was recognized, the significance was assessed at $P<0.05$ using Student-Newman-Keuls Test.

3) Experimental Example 1

Passive Avoidance Test 1

A passive avoidance test apparatus was prepared for the experiment. The passive avoidance test apparatus was divided into a first space and a second space, a guillotine door was placed between the two spaces, and the first and second spaces are connected by the door. The first space was kept light using illumination, and the second space was kept dark. The floor of the second space kept dark was provided with a grid, and an electric shock of 0.5 mA was applied for 3 seconds through the grid on the floor when the experimental animal moved to the dark space.

The mice prepared in the above section 1) were divided into 7 groups including drug administration groups 1 to 4, to which spinosin was to be administered, and control groups 1 to 3 (10 mice per group). The spinosin of Example 2 was dissolved in 10% Tween 80 (Polyoxyethylene sorbitan monooleate: Sigma, U.S.A.) and administered to drug administration groups 1 to 4 at doses of 2.5 mg/Kg, 5 mg/Kg, 10 mg/Kg, and 20 mg/Kg. Meanwhile, conepezil (Sigma-Aldrich Chemistry Co.) was administered to control group 1 at a dose of 5 mg/Kg, and 10% Tween 80 was administered to control groups 2 and 3 at a dose of 0.15 mL.

After about 30 minutes, scopolamine (Sigma-Aldrich Chemistry Co.) dissolved in distilled water was intraperitoneally administered to drug administration groups 1 to 4 and control groups 1 and 2 at a dose of 1 mg/Kg (Ebert, U. et al., Eur. J. Clin. Invest., 28, pp 944-949, 1998), and 0.9% saline solution was intraperitoneally administered to control group 3. After 30 minutes, learning about the passive avoidance test apparatus was performed on the mice in drug administration groups 1 to 4 and control groups 1 to 3, respectively. Specifically, the mice were placed in the first space kept light, and after a seek time of about 20 seconds, the guillotine door was opened, and the latency time taken for the mice to move to the second space kept dark was measured.

The mice that did not move to the second space kept dark until 60 seconds elapsed after the guillotine door was opened were excluded from the experiment.

After 24 hours since the learning was completed, the present experiment was performed on drug administration groups 1 to 4 and control groups 1 to 3, respectively. The latency tire taken for all four feet of the mouse to enter the dark space after the guillotine door was opened from the seek time of 10 seconds was measured up to 300 seconds. A longer latency time represents that the learning and memory of the passive avoidance is better.

In learning and in the present experiment, the average latency times of the mice in each group are shown in the following Table 1 and FIG. 1:

TABLE 1

| Experimental Group | Learning (sec) | Present Experiment (sec) |
|---|---|---|
| Drug administration group 1 (2.5 mg/Kg) | 25.88 ± 13.72 | 59.13 ± 46.88 |
| Drug administration group 2 (5 mg/Kg) | 29.38 ± 18.17 | 107.1 ± 91.70 |
| Drug administration group 3 (10 mg/Kg) | 20.50 ± 9.196 | 131.3 ± 69.94 |
| Drug administration group 4 (20 mg/Kg) | 36.00 ± 16.45 | 146.0 ± 83.53 |
| Control group 1 (donepezil) | 25.13 ± 13.68 | 151.9 ± 37.24 |
| Control group 2 | 26.50 ± 18.16 | 41.33 ± 18.92 |
| Control group 3 | 29.17 ± 18.15 | 300 |

Figure 1:
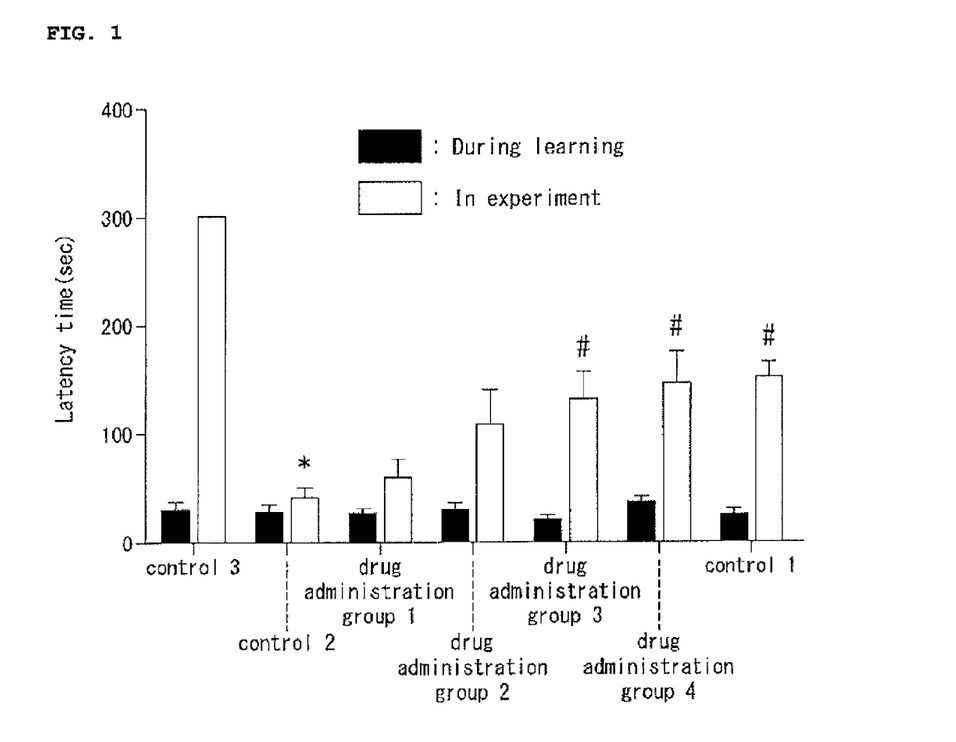
FIG. 1 shows the effect of a pharmaceutical composition comprising spinosin according to the present invention on the improvement of memory and learning ability.

As can be seen from Table 1 and FIG. 1, the latency time taken for the mice in drug administration groups 1 to 4, to which the spinosin prepared in Example 2 was administered, to move the second space was significantly increased compared to that in control group 2 to which only scopolamine was administered. Specifically, the latency time in drug administration group 1, to which the spinosin was administered at a dose of 2.5 mg/Kg, was increased about 20 seconds compared to that in control group 2, and the latency time in drug administration group 2, to which the spinosin was administered at a dose of 5 mg/Kg, was increased about 2.5 times compared to that in control group 2. Moreover, the latency time in drug administration group 3, to which the spinosin was administered at a dose of 10 mg/Kg, was increased about 3 times, compared to that in control group 2, and the latency time in drug administration group 4, to which the spinosin was administered at a dose of 20 mg/Kg, was increased about 3.5 times compared to that in control group 2. Particularly, it could be seen that the memory and learning ability of the mice with memory impairment induced by scopolamine in drug administration groups 3 and 4 was improved to an extent similar to that in control group 1 to which donepezil was administered.

It can be seen from these results that the spinosin prepared in Example 2 can effectively prevent or treat cognitive impairments such as dementia.

4) Experimental Example 2

Passive Avoidance Teat 2

The passive avoidance test was performed on drug administration groups 1 to 4 and control groups 1 to 3 by the same method as Experimental Example 1, except that the zizyphi spinosi semen extract extracted with 70% ethanol in Example 1 was dissolved in 10% Tween 80 and administered to drug administration groups 1 to 4 at doses of 25 mg/kg, 50 mg/kg, 100 mg/kg, and 200 mg/kg.

The results of the experiment are shown in the following Table 2 and FIG. 2:

TABLE 2

| Experimental Group | Learning (sec) | Present Experiment (sec) |
|---|---|---|
| Drug administration group 1 (25 mg/Kg) | 25.75 ± 15.92 | 49.50 ± 46.26 |
| Drug administration group 2 (50 mg/Kg) | 23.25 ± 18.17 | 40.00 ± 17.51 |
| Drug administration group 3 (100 mg/Kg) | 32.13 ± 18.92 | 173.9 ± 77.84 |
| Drug administration group 4 (200 mg/Kg) | 27.75 ± 19.00 | 112.8 ± 89.67 |
| Control group 1 (donepezil) | 17.25 ± 5.365 | 140.5 ± 25.47 |
| Control group 2 | 32.80 ± 21.26 | 26.10 ± 25.27 |
| Control group 3 | 21.00 ± 8.380 | 228.7.00 ± 50.65 |

Figure 2:
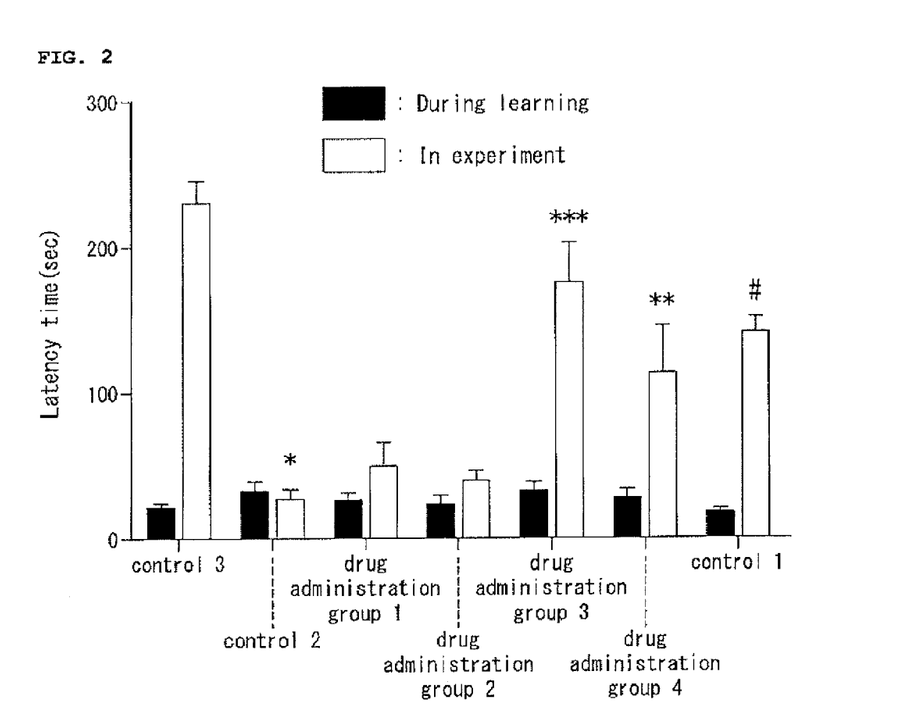
FIG. 2 shows the latency time for the mice in drug administration groups 1 to 4, to which the spinosin-containing zizyphi spinosi semen extract prepared in Example 1 was administered.

As can be seen from Table 2 and FIG. 2, the latency time taken for the mice in drug administration groups 1 to 4, to which the spinosin-containing zizyphi spinosi semen extract prepared in Example 1 was administered, to move the second space was significantly increased compared to that in control group 2 to which only scopolamine was administered. Specifically, the latency time in drug administration groups 1 and 2, to which the spinosin was administered at doses of 25 mg/Kg and 50 mg/Kg, respectively, was increased about 2 times compared to that in control group 2. Moreover, the latency time in drug administration group 3, to which the spinosin was administered at a dose of 100 mg/Kg, was increased about 6 times compared to that in control group 2, and the latency time in drug administration group 4, to which the spinosin was administered at a dose of 200 mg/Kg, was increased about 4.3 times compared to that in control group 2. Particularly, it could be seen that the memory and learning ability of the mice with memory impairment induced by scopolamine in drug administration groups 3 and 4 was improved to an extent similar to that in control group 1 to which donepezil was administered.

It can be seen from these results that the spinosin-containing zizyphi spinosi semen extract prepared in Example 1 can effectively prevent or treat cognitive impairments such as dementia.

5) Experimental Example 3

Y-Maze Test

A Y-maze was prepared for the experiment. The Y-maze had three arms, in which each arm was 42 cm in length, 3 cm in width, and 12 cm in height, the angle formed by three arms was 120 degrees, and the Y-maze was made of black polyvinyl resin.

The mice prepared in the above section 1) were divided into 5 groups including drug administration groups 1 and 2, to which the zizyphi spinosi semen extract prepared in Example 1 was to be administered, and control groups 1 to 3 (10 mice per group).

160 mg of the zizyphi spinosi semen extract of Example 1 was dissolved in 4 mL of 10% Tween 80 (Polyoxyethylene sorbitan monooleate: Sigma, U.S.A.) and administered to drug administration groups 1 and 2 at doses of 100 mg/Kg and 200 mg/Kg. Meanwhile, donepezil (Sigma-Aldrich Chemistry Co.) was administered to control group 1 at a dose of 5 mg/Kg, and 10% Tween 80 was administered to control groups 2 and 3 at a dose of 0.15 mL.

After about 30 minutes, scopolamine (Sigma-Aldrich Chemistry Co.) dissolved in distilled water was intraperitoneally administered to drug administration groups 1 and 2 and control groups 1 and 2 at a dose of 1 mg/Kg (Ebert, U. et al., Eur. J. Clin. Invest., 28, pp 944-949, 1998), and 0.9% saline solution was intraperitoneally administered to control group 3.

After 30 minutes, the mice in drug administration groups 1 and 2 and control groups 1 to 3 were carefully placed on one of three arms of the Y-maze, divided into A, B, and C, respectively, and allowed to freely move, and then the arms where the mice entered were recorded. At this time, only the case where the mouse' tail fully entered the arm was recorded as the arm where the experimental animal entered, and the case where the mouse entered the same arm was also recorded.

1 point was given to the case where the mouse sequentially entered three different arms (actual alternation). Alternation behavior was defined as the case where the mouse entered all three arms and was converted into a percentage (%) by the following Formula 1 (Sarter, M. et al., Psychopharmacology, 94, pp 491-495, 1998).

$$\text{Alternation behavior (\%)} = \frac{\text{Actual alternation}}{\text{Maximum alternation}} \times 100 \quad \text{[Formula 1]}$$

(Maximum alternation: Total entry – 2)

The alternation behaviors converted by the above Formula 1 are shown in the following Table 3 and FIG. 3, and the total entries, each representing the total number of entries, are shown in the following Table 4 and FIG. 4:

TABLE 3

| Experimental Group | Alternation behavior (%) |
|---|---|
| Drug administration group 1 (100 mg/Kg) | 63.32 ± 9.005 |
| Drug administration group 2 (200 mg/Kg) | 60.91 ± 6.369 |
| Control group 1 (Donepozil) | 65.71 ± 10.19 |
| Control group 2 | 50.92 ± 14.59 |
| Control group 3 | 76.53 ± 8.379 |

TABLE 4

| Experimental Group | Total entry |
|---|---|
| Drug administration group 1 (100 mg/Kg) | 37.00 ± 14.30 |
| Drug administration group 2 (200 mg/Kg) | 32.30 ± 7.675 |
| Control group 1 (Donepezil) | 34.75 ± 7.265 |
| Control group 2 | 24.75 ± 6.519 |
| Control group 3 | 26.88 ± 13.78 |

Figure 3:
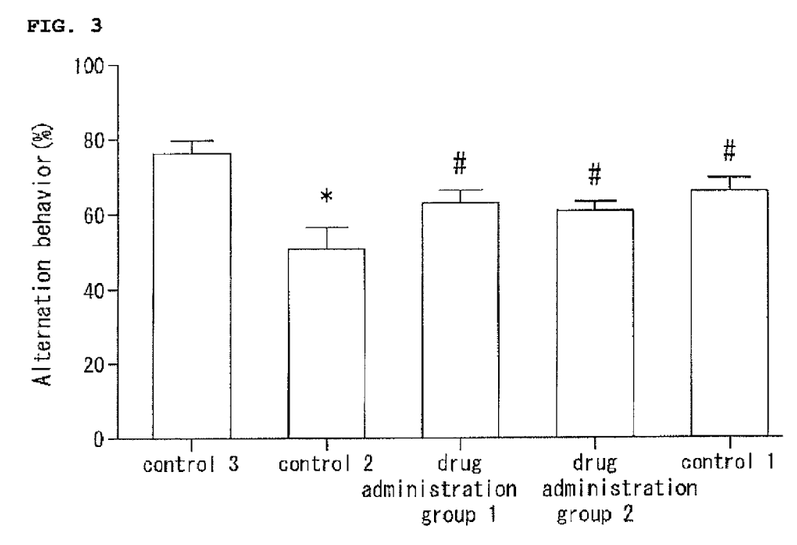
FIG. 3 shows the alternation behaviors in a Y-maze test for mice in drug administration groups 1 and 2, to which the spinosin-containing zizyphi spinosi semen extract prepared in Example 1 was administered.
Figure 4:
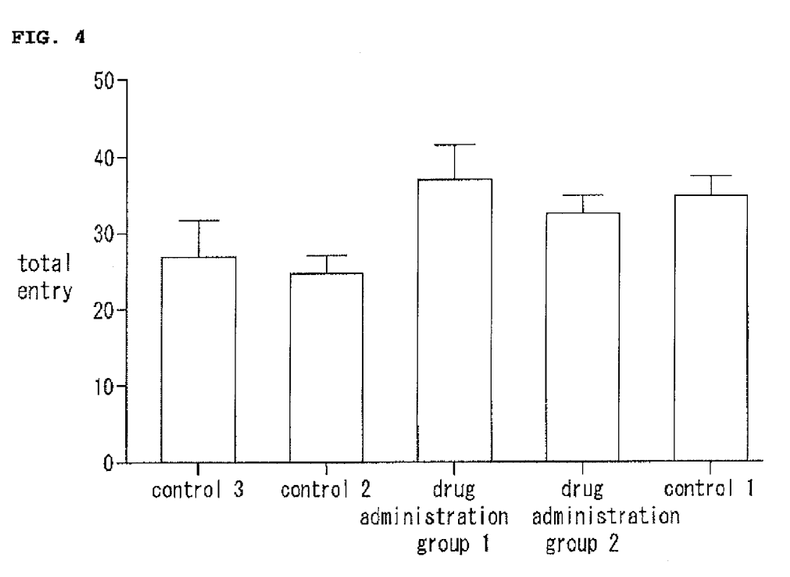
FIG. 4 shows the total entries of the arms of a Y-maze test for mice in drug administration groups 1 and 2 and control groups 1 to 3.

As can be seen from Table 3 and FIG. 3, the alternation behaviors in drug administration groups 1 and 2, to which the spinosin-containing zizyphi spinosi semen extract prepared in Example 1 was administered, were increased compared to those in control group 2, to which only scopolamine was administered, and were similar to those in control group 1 to which donepezil was administered. Moreover, as can be seen from Table 4 and FIG. 4, the total entries in drug administration groups 1 and 2 and control groups 1 to 3 were all similar to each other. Therefore, it could be seen that the increase in the alternation behavior did not result from the change in the activity of the mice, and thus it could be seen that the memory and learning ability of the mice in drug administration groups 1 and 2 was significantly improved by the spinosin-containing zizyphi spinosi semen extract prepared in Example 1.

It can be seen from these results that the spinosin-containing zizyphi spinosi semen extract prepared in Example 1 can effectively prevent or treat cognitive impairments such as dementia.

6) Experimental Example 4

Morris Water Maze Test

A Morris water maze test apparatus was prepared for the experiment. Four labels such as star, square, triangle, and circle were put at regular intervals on a circular pool of 90 cm in diameter and 45 cm in height, and a platform of 29 cm in height was positioned below the star. Water was filled up to 0.5 cm from the platform (water temperature: 21±1° C.) and became cloudy with pigment such that the platform was not visible from the surface of the water.

The mice prepared in the above section 1) were divided into 5 groups including drug administration groups 1 and 2, to which the zizyphi spinosi semen extract prepared in Example 1 was to be administered, and control groups 1 to 3 (10 mice per group).

160 mg of the zizyphi spinosi semen extract of Example 1 was dissolved in 4 mL of 10% Tween 80 (Polyoxyethylene sorbitan monooleate: Sigma, U.S.A.) and administered to drug administration groups 1 and 2 at doses of 100 mg/Kg and 200 mg/Kg. Meanwhile, donepezil (Sigma-Aldrich Chemistry Co.) was administered to control group 1 at a dose of 5 mg/Kg, and 10% Tween 80 was administered to control groups 2 and 3 at a dose of 0.15 mL.

After about 30 minutes, scopolamine (Sigma-Aldrich Chemistry Co.) dissolved in distilled water was intraperitoneally administered to drug administration groups 1 and 2 and control groups 1 and 2 at a dose of 1 mg/Kg (Ebert, U. et al., Eur. J. Clin. Invest., 28, pp 944-949, 1998), and 0.9% saline solution was intraperitoneally administered to control group 3.

After 30 minutes, the time taken for the mice, put down in one section of the pool, in drug administration groups 1 and 2 and control groups 1 to 3 to reach the platform was measured for 60 seconds. After 30 minutes, the time taken for the mice, repositioned to the original position, to reach the platform was measured until 60 seconds. The above-described process was repeated 4 times, and the average values were obtained. The experiment was performed in the same manner as on the first day while administering the drugs for 4 days, except that the position where the mice were first put down was changed.

The results of the experiment are shown in the following Table 5 and FIG. 5:

TABLE 5

| Experimental group | Time (sec) | | | |
|---|---|---|---|---|
| | $1^{st}$ day | $2^{nd}$ day | $3^{rd}$ day | $4^{th}$ day |
| Drug administration group 1 (100 mg/Kg) | 56.10 ± 9.088 | 59.85 ± 0.4743 | 49.85 ± 16.64 | 46.70 ± 15.96 |
| Drug administration group 2 (200 mg/Kg) | 52.75 ± 12.17 | 46.20 ± 12.52 | 43.45 ± 18.19 | 30.55 ± 20.45 |
| Control group 1 (Donepezil) | 59.34 ± 2.055 | 48.75 ± 14.98 | 42.80 ± 15.16 | 34.35 ± 13.80 |
| Control group 2 | 57.75 ± 7.115 | 57.05 ± 6.693 | 53.95 ± 11.13 | 57.30 ± 6.701 |
| Control group 3 | 57.10 ± 6.736 | 40.35 ± 14.98 | 27.65 ± 16.27 | 25.60 ± 13.70 |

Figure 5:
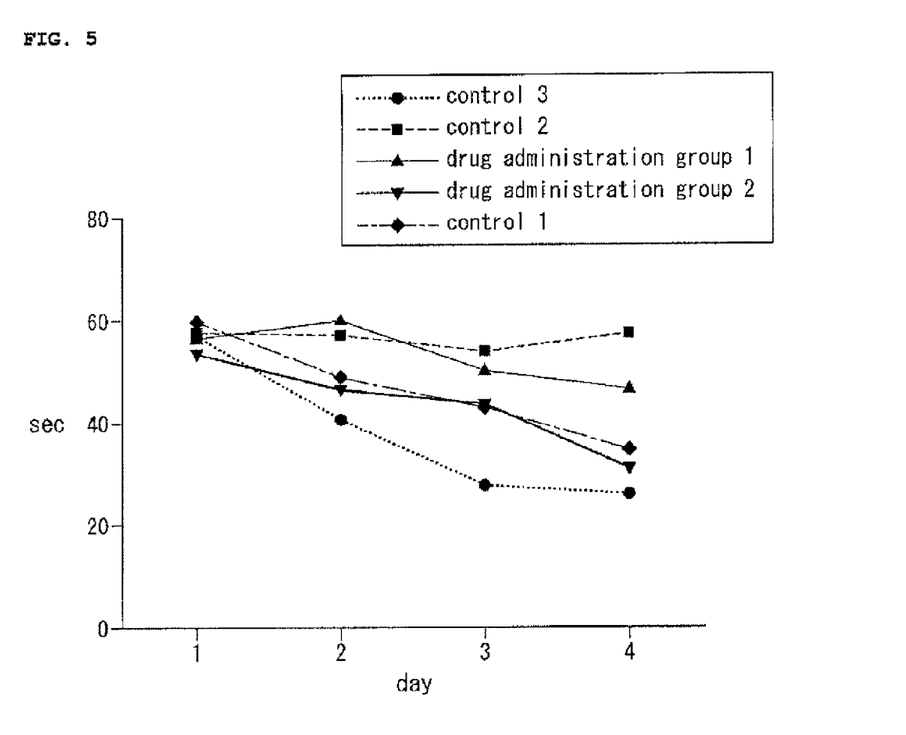
FIG. 5 shows the time taken for the mice in drug administration groups 1 and 2, to which the spinosin-containing zizyphi spinosi semen extract prepared in Example 1 was administered, to reach the platform in a Morris water maze test.

As can be seen from Table 5 and FIG. 5, the time taken for the mice in drug administration groups 1 and 2, to which the spinosin-containing zizyphi spinosi semen extract prepared in Example 1 was administered, to reach the platform was reduced by more than 10 seconds and 25 seconds, respectively, on the $3^{rd}$ and $4^{th}$ day compared to that in control group 2 to which only scopolamine was administered. Particularly, in the case of drug administration group 2, the time taken for the mice to reach the platform was reduced compared to that in control group 1 to which donepezil was administered, indicating that the spinosin-containing zizyphi spinosi semen extract prepared in Example 1 had superior memory and learning ability to the donepezil.

Preparation of Formulations and Food Compositions

Preparation of Powders

Powders were prepared by mixing 20 mg of the spinosin-containing zizyphi spinosi semen extract prepared in Example 1, 100 mg of lactose, and 10 mg of talc and packing the mixture in airtight bags.

Preparation of Tablets

Tablets were prepared using the spinosin-containing zizyphi spinosi semen extract prepared in Example 1 and the ingredients shown in the following Table 6:

TABLE 6

| Ingredients | Content (mg) |
| --- | --- |
| Zizyphi spinosi semen extract (Example 1) | 10 |
| Corn starch | 100 |
| Lactose | 100 |
| Magnesium stearate | 2 |

Tablets were prepared by mixing the above ingredients and compressing the mixture into tablets according to a conventional method for preparing tablets.

Preparation of Capsules

TABLE 7

| Ingredients | Content (mg) |
| --- | --- |
| Zizyphi spinosi semen extract (Example 1) | 10 |
| Crystalline cellulose | 100 |
| Lactose | 100 |
| Magnesium stearate | 0.2 |

Capsules were prepared by mixing the above ingredients and filling the mixture in gelatin capsules according to a conventional method for preparing capsules.

Preparation of Injections

TABLE 8

| Ingredients | Content (mg) |
| --- | --- |
| Zizyphi spinosi semen extract (Example 1) | 10 |
| Mannitol | 180 |
| Sterile distilled water for injection | 2974 |
| $Na_2HPO_4 \cdot 12H_2O$ | 26 |

Injections were prepared by mixing the above ingredients JO to prepare a solution and filling the solution in ampoules (2 mL), followed by sterilization, according to a conventional method for preparing injections.

Preparation of Liquid Formulations

TABLE 9

| Ingredients | Content |
| --- | --- |
| Zizyphi spinosi semen extract (Example 1) | 20 mg |
| Isomerized sugar | 10 g |
| Mannitol | 5 g |
| Purified water | 85 ml |

Liquid formulations were prepared by dissolving the above ingredients in purified water, adding a suitable amount of lemon flavor, adding purified water to the mixture to prepare a solution of 100 ml, and loading the solution into brown bottles, followed by sterilization, according to a conventional method for preparing liquid formulations.

Preparation of Health Foods

TABLE 10

| Ingredients | Content |
| --- | --- |
| Zizyphi spinosi semen extract (Example 1) | 1000 mg |

TABLE 10-continued

| Ingredients | Content |
| --- | --- |
| Nicotinic acid amide | 1.7 mg |
| Folic acid | 50 µg |
| Calcium pantothenate | 0.5 mg |
| Ferrous sulfate | 1.75 mg |
| Zinc oxide | 0.82 mg |
| Magnesium carbonate | 25.3 mg |
| Potassium Phosphate monobasic | 15 mg |
| calcium Phosphate dibasic | 35 mg |
| Potassium citrate | 90 mg |
| Calcium carbonate | 100 mg |
| Magnesium chloride | 24.8 mg |
| Vitamin mixture | Suitable amount |
| Mineral mixture | Suitable amount |

Health food compositions were prepared according to a conventional method by mixing the above ingredients according to a conventional method for preparing health foods and then preparing granules.

Preparation of Health Beverages

TABLE 11

| Ingredients | Content |
| --- | --- |
| Zizyphi spinosi semen extract (Example 1) | 1000 mg |
| Citric acid | 1000 mg |
| Oligosaccharide | 100 g |
| Japanese apricot concentrate | 2 g |
| Taurine | 1 g |
| Purified water | Total 900 mL |

Health beverages were prepared by dissolving the above ingredients in purified water to prepare a solution of a 900 mL, stirring and heating the solution at 85° C. for about 1 hour, filtering the solution, filling the solution in sterilized 2 L bottles, sealing and sterilizing the bottles, and keeping the bottles under refrigeration according to a conventional method for preparing health beverages.

The invention claimed is:

1. A method of treatment of dementia, comprising administering in an amount effective to treat dementia to a subject in need thereof a pharmaceutical composition comprising spinosin or a pharmaceutical acceptable salt thereof, as an active ingredient.

2. The method of claim 1, wherein the composition further comprises a pharmaceutically acceptable additive.

3. A method of treatment of dementia, comprising administering in an amount effective to treat dementia to a subject in need thereof a pharmaceutical composition comprising spinosin, wherein the pharmaceutical composition comprises at least one selected from the group consisting of an extract of *Zizyphus jujuba* Mill var. *inermis*, an extract of *Zizyphus jujuba* Mill var. *hoonensis*, an extract of *Zizyphus jujuba* Mill var. *spinosa*, an extract of *Passiflora edulis flavicarpa*, an extract of *Cayaponia tayuya*, an extract of *Desmodium tortuosum*, an extract of *Wilbrandia ebracteata*, an extract of *Strophioblachia fimbricalyx*, an extract of *Clutia abyssinica* and an extract of *Saccharopolyspora spinosa*.

4. The method of claim 3, wherein the pharmaceutical composition includes an extract of the seed of *Zizyphus jujube* Mill var. *spinosa*.

5. The method of claim 3, wherein the composition further comprises a pharmaceutically acceptable additive.

* * * * *